(12) United States Patent
Kim et al.

(10) Patent No.: US 8,980,863 B2
(45) Date of Patent: Mar. 17, 2015

(54) MODULATION OF RADIATION RESPONSE USING MICRORNA

(71) Applicant: SNU R&DB Foundation, Seoul (KR)

(72) Inventors: In-Ah Kim, Seongnam-si (KR); Bong-Jun Cho, Yongin-si (KR); Eun Jung Choi, Seoul (KR); Hans Hyonchang Kim, Syracuse, NY (US); David J. Lee, Las Vegas, NV (US)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/888,624

(22) Filed: May 7, 2013

(65) Prior Publication Data

US 2014/0194488 A1    Jul. 10, 2014

(30) Foreign Application Priority Data

Jan. 8, 2013 (KR) ......................... 10-2013-0002239

(51) Int. Cl.
*A61K 48/00* (2006.01)
*A61K 31/7105* (2006.01)

(52) U.S. Cl.
CPC .................................. *A61K 31/7105* (2013.01)
USPC .......................................... 514/44; 536/24.5

(58) Field of Classification Search
CPC ................................................ C12N 2310/141
See application file for complete search history.

(56) References Cited

U.S. PATENT DOCUMENTS

2006/0105360 A1 * 5/2006 Croce et al. ...................... 435/6

FOREIGN PATENT DOCUMENTS

KR    10-2012-0070626    6/2012

OTHER PUBLICATIONS

Wu et al. (LPoS One Jan. 2011: e16264).*
Fokas et al. (Thoracic Cancer 2010; 153-162).*
Novakova et al. (Biochem and Biophysical Res Comm 2009, 1-5).*
I. Kim et al., "MicroRNA-200c Increases Radiosensitivity of Human Cancer Cells With Activated EGFR or HER2-associated Signaling," Dept of Radiation Oncology, National University Bundang Hospital (Oct. 28, 2012).
Gong Chen et al., "MicroRNA-181a sensitizes human malignant glioma U87MG cells to radiation by targeting Bcl-2". Oncology Reports. vol. 23, pp. 997-1003 (Apr. 2010).
Sanjay K. Singh et al., "A microRNA Link to Glioblastoma Heterogeneity". Cancers. vol. 4, pp. 846-872 (Sep. 2012).
Sajani S. Lakka, "MicroRNA 203 modulates glioma cell migration and invasion by targeting ROBO1" Cancer Research. 2012. vol. 72, Issue 8, Supplement 1. Abstract 5621 (Apr. 2012).

* cited by examiner

*Primary Examiner* — Kimberly Chong
(74) *Attorney, Agent, or Firm* — Lexyoume IP Meister, PLLC

(57) ABSTRACT

The present invention relates to a technology of enhancing sensitivity to radiotherapy using microRNA, more particularly to a radiosensitizer composition comprising at least one selected from the group consisting of microRNA-26b, microRNA-203 and microRNA-200c, an anticancer supplement, and a method for enhancing sensitivity to radiotherapy of cancer cells using the same.

10 Claims, 3 Drawing Sheets
(2 of 3 Drawing Sheet(s) Filed in Color)

MODULATION OF RADIATION RESPONSE USING MICRORNA

CROSS REFERENCE TO RELATED APPLICATION

This application claims priority to and the benefit of Korean Patent Application No. 10-2013-0002239 filed on Jan. 8, 2013, which is hereby incorporated by reference for all purposes as if fully set forth herein.

BACKGROUND OF THE INVENTION

1. Field of the Invention

The present invention relates to a technology of enhancing radiosensitivity using microRNA, more particularly to a radiosensitizer composition comprising at least one selected from the group consisting of microRNA-26b, microRNA-203 and microRNA-200c, an anticancer supplement, and a method for enhancing radiosensitivity of cancer cells using the same.

2. Description of the Related Art

Cancer therapy may be largely classified into surgery, radiotherapy, and chemotherapy. Among them, radiotherapy is currently known as an essential treatment method in various kinds of cancer, but several problems have been pointed out, including radioresistance acquisition of cancer cells, decrease in radiotherapy effect due to normal tissue damage by high dose radiotherapy, and the like. Thus, many studies are conducted on radiosensitizer for enhancing the effect of radiotherapy.

As radiosensitizer reported to date, anticancer drugs such as taxol or cysplatin are known, but they have limitations in practical use because toxicity of anticancer drugs may be exhibited complicatedly with side effects of radiotherapy including inflammation at the site of radiotherapy, gastrointestinal disorder, nausea, vomiting, and the like, when combined with radiotherapy. And, as radiotherapy enhancer that is used only for radiotherapy without properties as anticancer drugs, tirapazamine is known, but it has effect only on tumor cells with hypoxia, and is known to have an insignificant effect in clinical radiotherapy because drug delivery into tumor tissue is insufficient due to internal pressure of tumor, which is intrinsic to hypoxia. In addition, although there have been many attempts to develop drugs for increasing radiotherapy effect, only extremely few drugs may be used in practical patient treatment, and unexpected resistance problem is being raised in a part of the existing successful drugs. Thus, there is demand for development of a radiosensitizing method specifically acting on cancer cells.

Particularly, in the treatment of brain tumor, radiotherapy is important as well as surgery and anticancer therapy. Since brain tumor such as malignant glioma (GBM) has properties of high proliferation rate, hypoxia, angiogenesis, brain infiltration, and high cancer recurrence rate, there is a limitation with chemotherapy. Although radiotherapy may induce cell cycle delay or cell death through DNA damage in the cells by radiation to remove abnormal cells, due to intrinsic radioresistance of cancer cells and resistance increase according to radiotherapy, radioresistant cancer cells may induce cancer recurrence and they may also become resistant to anticancer drugs. Thus, there is urgent need for development of radiosensitivity enhancer that may enhance radiosensitivity of cancer cells with intrinsic radioresistance, minimize side effect, and optimize radiotherapy effect through delay in the repair of DNA damage induced by radiation in the cells.

Meanwhile, microRNA (or miRNA) refers to nonprotein-coding RNA that controls expression of various genes, and it inhibits translation of mRNA, or post-transcriptionally inhibits gene expression by inducing decomposition of mRNA. The post-transcriptional regulation is used as a strong regulation method in the process requiring exact and detailed gene expression such as intracellular signal transfer, and since about half of gene expression changes due to external stimulation are post-transcriptionally regulated, the post-transcriptional regulation is reported to play a very important function in the regulation of total gene expression. It was found through several studies that microRNA plays an important function of regulating many biological processes such as cell differentiation, proliferation, cell death, cytogenesis, immune, metabolism and stem cell maintenance, and the like. It was also found that several microRNAs function as tumor inducer or tumor inhibitor.

As the results of studies on correlationship between expression levels of microRNA-7, microRNA-26b, microRNA-203 and microRNA-200c and radioresistance in brain tumor cell, glioma cells, the inventors found out that the microRNAs may effectively increase radiosensitivity of cancer cells through delay in the repair of DNA damage by radiation. Thus, the present invention is based on the discovery that these microRNAs may enhance radiosensitivity of cancer cells having intrinsic radioresistance to maximize radiotherapy effect, and they may be also applied for an anticancer supplement.

SUMMARY OF THE INVENTION

It is an object of the present invention to discover novel microRNA that may enhance radiosensitivity in cancer cells with intrinsic radioresistance to radiotherapy, and to provide a radiosensitizer and an anticancer supplement comprising the microRNA as an active ingredient.

More specifically, it is an object of the present invention to provide a sensitizer composition for radiotherapy of brain tumor, comprising at least one selected from the group consisting of micoRNA-26b, microRNA-203 and microRNA-200c.

It is another object of the present invention to provide an anticancer supplement composition for radiotherapy of brain tumor, comprising at least one selected from the group consisting of micoRNA-26b, microRNA-203 and microRNA-200c.

It is still another object of the present invention to provide a method for enhancing radiosensitivity of brain tumor cells, comprising treating brain tumor cells with at least one selected from the group consisting of microRNA-26b, microRNA-203 and microRNA-200c.

It is still another object of the present invention to provide a method for enhancing radiosensitivity of a brain tumor patient, comprising administering a therapeutically effective amount of at least one selected from the group consisting of microRNA-26b, microRNA-203 and microRNA-200c to a brain tumor patient.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE PREFERRED EMBODIMENTS

Figure 1:
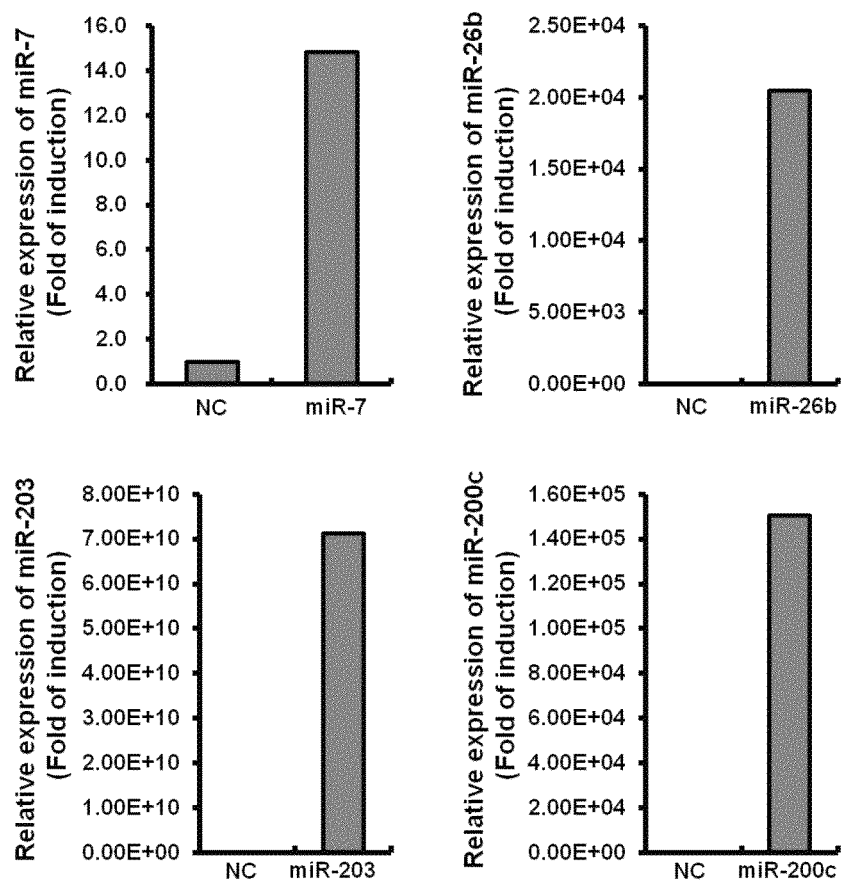
FIG. 1 shows the results of measuring the amount of expression of mature microRNA of each microRNA when microRNA-7, microRNA-26b, microRNA-203 and microRNA-200c are respectively introduced in U251 cells to induce transformation, and then, the cells are irradiated.

According to one embodiment, the present invention relates to a sensitizer composition for radiotherapy of brain tumor, comprising at least one selected from the group consisting of microRNA-26b, microRNA-203 and microRNA-200c. Preferably, the composition may further comprise microRNA-7.

According to another embodiment, the present invention relates to an anticancer supplement composition for radiotherapy of brain tumor, comprising at least one selected from the group consisting of microRNA-26b, microRNA-203 and microRNA-200c. Preferably, the composition may further comprise microRNA-7.

According to yet another embodiment, the present invention relates to a method for enhancing radiosensitivity of brain tumor cells, comprising treating brain tumor cells with at least one selected from the group consisting of microRNA-26b, microRNA-203 and microRNA-200c. Preferably, the method may further comprise a step of treating brain tumor cells with microRNA-7.

According to yet another embodiment, the present invention relates to a method for enhancing radiosensitivity of a brain tumor patient, comprising administering a therapeutically effective amount of at least one selected from the group consisting of microRNA-26b, microRNA-203 and microRNA-200c to a brain tumor patient. Preferably, the method may further comprise a step of administering a therapeutically effective amount of microRNA-7.

Hereinafter, the present invention will be explained in detail.

In the present invention, the microRNA-7, microRNA-26b, microRNA-203 and microRNA-200c may be derived from animals including human, for example, monkey, pig, horse, cow, sheep, dog, cat, mouse, rabbit, and the like, preferably human.

The nucleic acid molecule making up the microRNA-7, microRNA-26b, microRNA-203 and microRNA-200c of the present invention may respectively have a length of 18 to 100 nt (nucleotide). According to preferable embodiment, the nucleic acid molecule may be provided in the form of mature microRNA of 19 to 25 nt length, more preferably 21, 22 or 23 nt length. And, according to another preferred embodiment, it may be provided in the form of precursor microRNA of 50 to 100 nt length, more preferably, 65-95 nt length.

The base sequence information of the microRNA-7, microRNA-26b, microRNA-203 and microRNA-200c nucleic acid molecules in the form of mature microRNA or precursor microRNA may be confirmed in known gene database such as miRBASE (http://www.mirbase.org/). More specifically, base sequence of the mature form of microRNA-7 is registered as gene registration No. MIMAT0000252 (SEQ ID NO. 1), and the precursor form is registered as MI0000263 (SEQ ID NO. 2). The base sequence of the mature form of microRNA-26b is registered as gene registration No. MIMAT0000083 (SEQ ID NO. 3), and the precursor form is registered as MI0000084 (SEQ ID NO. 4). The base sequence of the mature form of microRNA-203 is registered as gene registration No. MIMAT0000264 (SEQ ID NO. 5), and the precursor form is registered as MI0000283 (SEQ ID NO. 6). The base sequence of the mature form of microRNA-200c is registered as gene registration No. MIMAT0004657 (SEQ ID NO. 7), and the precursor form is registered as MI0000650 (SEQ ID NO. 8).

And, the microRNA-7, microRNA-26b, microRNA-203 and microRNA-200c includes variants thereof that may be functionally equivalent to the microRNA nucleic acid molecules even if a part of the base sequence of the microRNA nucleic acid molecule is modified by deletion, substitution or insertion. For example, the microRNA of the present invention may exhibit 80% or more identity, preferably 90%, more preferably 95% or more identity with the base sequence of each corresponding SEQ ID NO. The identity may be easily determined by comparing the sequence of nucleotide with the corresponding part of target gene using computer algorithm well known in the art, for example Align or BLAST algorithm.

And, microRNA-7, microRNA-26b, microRNA-203 and microRNA-200c nucleic acid molecule of the preset invention may exist in the form of single strand or double strand. The mature microRNA molecule mainly exists as single strand, and the precursor microRNA molecule may include a partial self-complementary structure (for example, a stem-loop structure) that may form a double strand. And, the nucleic acid molecule of the present invention may be constituted in the form of RNA, PNA (peptide nucleic acids) or LNA (locked nucleic acid).

The nucleic acid may be separated or prepared by standard molecular biological techniques, for example, chemical synthesis or recombination, or those commercially available may be used, The microRNA-7, microRNA-26b, microRNA-203 and microRNA-200c, if administered in the body, may be involved in a pathway whereby microRNA is activated to function in the cells, to increase expression level of microRNA, or increase the activity. And, they may directly act on microRNA, or indirectly act on upstream modulator of microRNA, to increase expression of microRNA at transcription level, decrease decomposition of expressed microRNA, or increase the activity, thereby increasing the expression level or activity of microRNA.

Figure 2:
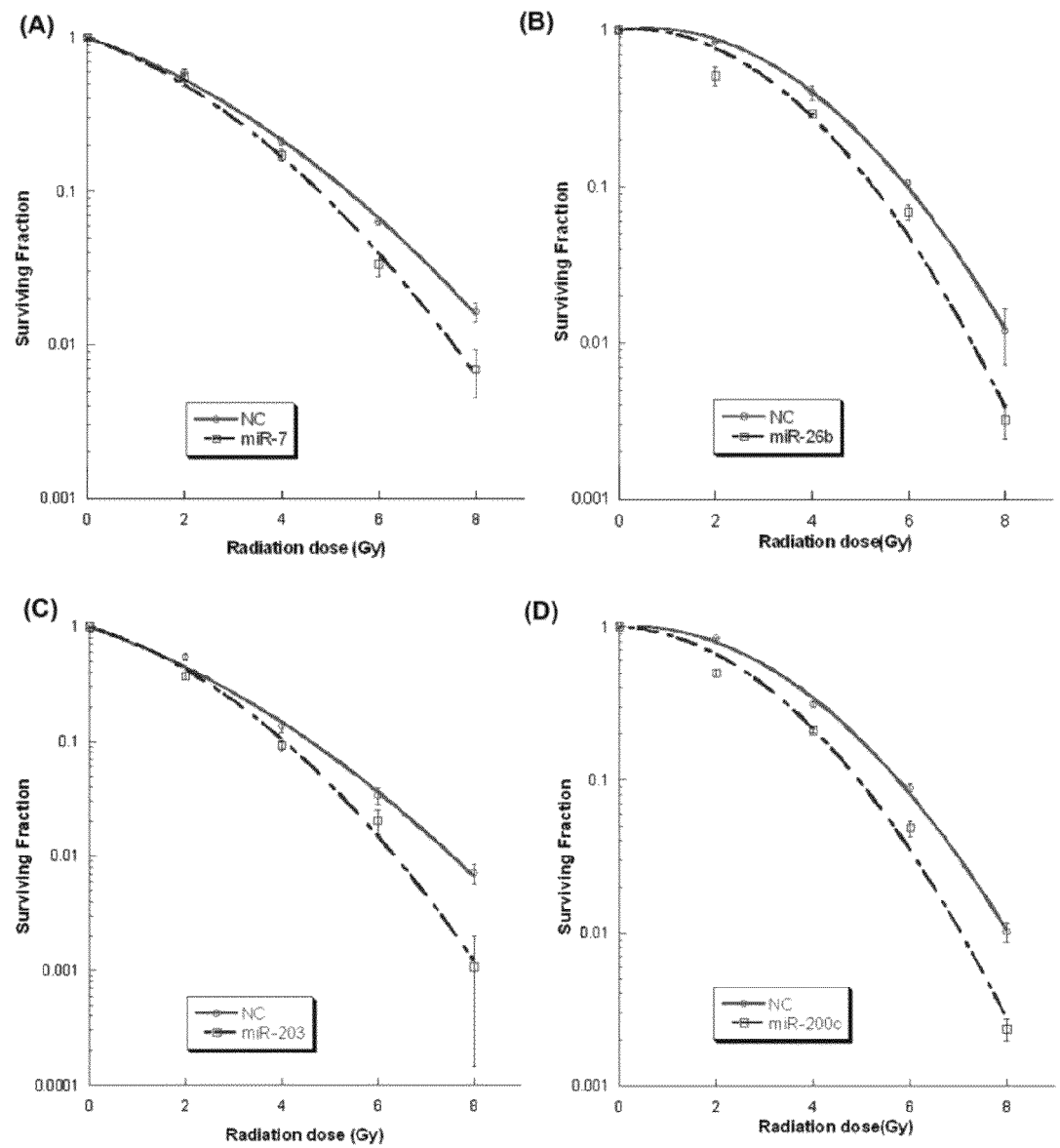
FIG. 2 shows the results of measuring viability of cell colony according to radiation dose, when microRNA-7 (FIG. 2A), microRNA-26b (FIG. 2B), microRNA-203 (FIG. 2C) and microRNA-200c (FIG. 2D) are respectively introduced in U251 cells to induce transformation, and then, the cells are irradiated.
Figure 3:
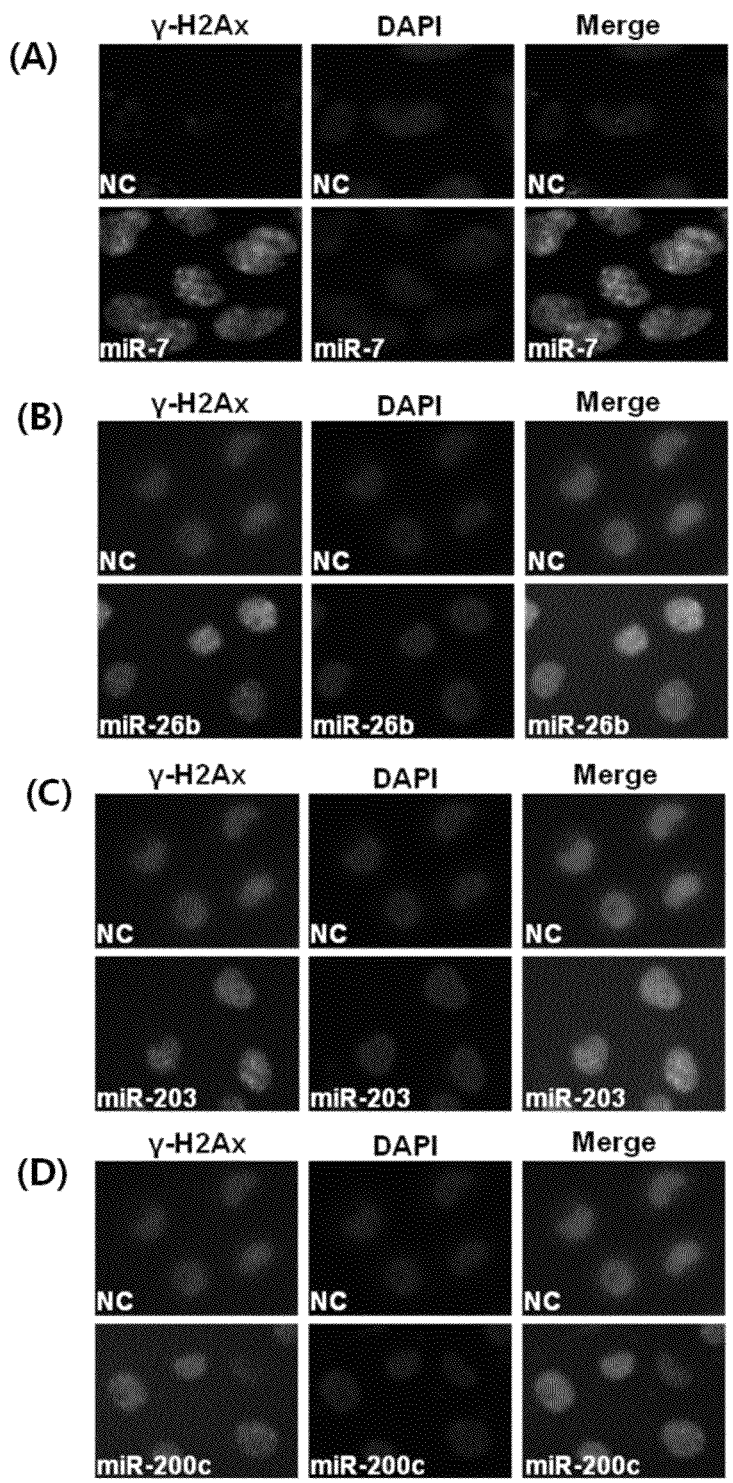
FIG. 3 show the effect of microRNA-7 (FIG. 3A), microRNA-26b (FIG. 3B), microRNA-203 (FIG. 3C) and microRNA-200c (FIG. 3D) on DNA damage mechanism and repair mechanism.

According to specific examples of the invention, it was confirmed that when microRNA-7, microRNA-26b, microRNA-203 and microRNA-200c are respectively introduced in brain tumor cell line U251 cells to induce transformation, and then, the cells are irradiated, the expression amount of each mature microRNA is largely increased, specifically microRNA-7 increases 14.8-fold, microRNA-26b increases 20.478-fold, microRNA-203 increases 71,285,641,482-fold, and microRNA-200c increases 15.298-fold (FIG. 1), and thereby, viability of cell colony decreases compared to control, thus confirming that radioresistance of cancer cells is decreased, namely, radiosensitivity is enhanced (FIG. 2). Furthermore, it was confirmed that repair of cancer cell DNA damage induced by radiation is inhibited and delayed (FIG. 3).

Thus, the microRNA-7, microRNA-26b, microRNA-203 and microRNA-200c may effectively increase radiosensitivity in cancer cells through inhibition and delay in repair of DNA damage induced by radiation, thereby optimizing anticancer therapy effect by radiation, and it may also act as an anticancer supplement.

As used herein, the term "radioresistance" refers to inability to kill abnormal cells or slight degree of killing them in spite of irradiation, in disease treatment using radiation. Alternatively, it refers to the case wherein there is no treatment effect from the beginning, or although there is treatment effect at the beginning, the treatment effect is lost during a continuous treatment process.

Radiotherapy may induce cell cycle delay or cell death through DNA damage in the cells by radiation to remove abnormal cells, but it has problems in that recurrence of cancer may be induced due to intrinsic radioresistance of cancer cells and the resulting increase in resistance to radiotherapy, and the cells may become resistant to anticancer drugs.

As used herein, the term "radiosensitizer" refers to an agent capable of enhancing sensitivity of cells to radiation in disease treatment using radiation. Thereby, raiotherapy efficiency may be increased, specifically, if it is treated in combination for cancer treatment, radiosensitivity of cancer cells may be enhanced to exhibit the effects of cancer cell killing and proliferation inhibition.

The kind of cancers for which the technology of the present invention may be applied is not specifically limited, but preferably, the present invention may be applied for brain tumor treatment. The brain tumor includes primary and metastatic brain tumor, malignant brain tumor, and histologically, includes glioma, astrocytoma, glioblastoma, medulloblastoma, meningioma, vestibular schwannoma, pituitary adenoma, and lymphoma, and the like. Preferably, it may be glioma.

According to one embodiment, the microRNA-7, microRNA-26b, microRNA-203 and microRNA-200c nucleic acid molecule may be introduced in the cells using various transformation techniques such as nucleic acid and DEAE-dextran complex, nucleic acid and nucleoprotein complex, nucleic acid and lipid complex, and the like. More specifically, it may be introduced in the cells together with G-fectin, Minis TrasIT-TKO lipophilic reagent, delivery reagent including lipofectin, lipofectamine, cellfectin, cationic phospholipid nanoparticles, cationic polymer, cationic micelle, cationic emulsion or liposome, or biocompatible polymer such as polyethyleneglycol may be conjugated therewith to increase intracellular absorption.

According to another embodiment, the microRNA nucleic acid may be included in a delivery system enabling efficient intracellular introduction. The delivery system may be preferably a vector, and both viral vector and non-viral vector may be used. The viral vector may include lentivirus, retrovirus, adenovirus, herpes virus and avipox virus vector, and the like may be used, but is not limited thereto.

The expression vector comprising the microRNA nucleic acid molecule may preferably further include a selection marker to allow easy selection of transformed cells. Specific examples of the markers may include those affording selectable phenotype such as drug resistance, auxotrophy, resistance to cytotoxic agent or surface protein expression, for example, green fluorescent protein, puromycin, neomycin, hygromycin, histidinol dehydrogenase (hisD) and guanine phosphoribosyltransferase (Gpt), and the like.

According to another embodiment, the microRNA nucleic acid molecule may be introduced in the cells. The cells in which the microRNA nucleic acid molecule is introduced may express microRNA with high level, and by implanting the cells into cancer tissues, radiosensitivity of cancer tissues may be enhanced and radiotherapy effect may be maximized.

According to more preferable embodiment, the microRNA may be provided together with tumor-specific targeting sequence so that it may be introduced only into tumor cells. The tumor-specific targeting sequence may include target molecules commonly known in the art, for example, molecules interacting with integrin, endothelial growth factor receptor, Ha-ras tumor gene product, p53, carcinoembryonal antigen (CEA), raf tumor gene product, gp100/pme17, GD2, GD3, GM2, TF, sTn, MAGE-1, MAGE-3, BAGE, GAGE, tyrosinase, gp75, melan-A/Mart-1, gp100, HER2/neu, EBV-LMP 1 & 2, HPV-F4, 6, 7, prostate specific antigen (PSA), HPV-16, HPV E7, MUM, alpha-fetoprotein (AFP), C017-1A, GA733, gp72, Wilm's tumor antigen-1, and telomerase, and the like, but is not limited thereto.

Meanwhile, the composition comprising the microRNA nucleic acid molecule of the present invention may further comprise a pharmaceutically acceptable carrier, and it may be formulated together with a carrier. The pharmaceutically acceptable carrier refers to a carrier or diluent that does not stimulate organisms and does not inhibit biological activity and property of administered compounds. As a pharmaceutically acceptable carrier for a composition formulated into a liquid solution, those suitable for body and sterilization may be used, and for example, a saline solution, sterilized water, a Ringer's solution, buffered saline, an albumin solution for injection, a dextrose solution, a malto dextrin solution, glycerol, ethanol, and a combination thereof may be used, and if necessary, other commonly used additives such as antioxidant, a buffered solution, a bacteriostatic agent, and the like may be added. And, the composition may be formulated in the form of a solution or suspension (for example, integrated with microparticles, liposome, or cells).

The composition comprising microRNA nucleic acid molecule and pharmaceutically acceptable carrier of the present invention may be applied in any dosage form containing the same as an active ingredient, and it may be formulated and administered in oral or parenteral dosage forms. The administration refers to introducing the pharmaceutical composition of the present invention into a patient by any appropriate method, and includes delivery of microRNA nucleic acid by viral or non-viral techniques or implantation of cells expressing microRNA. The composition of the present invention may be administered by various routes including oral or parenteral administration as long as it may reach target tissue, and preferably, it may be locally administered to cancer tissue.

The method for enhancing radiosensitivity and radiation treatment method of the present invention may be applied to any animals in which cancer may occur, and the animals may include domestic animals such as cows, pigs, sheep, horses, dogs, and cats, and the like, as well as human and primates.

The radiotherapy of the present invention includes administering the composition of the present invention to cancer cells, and irradiating the cells, wherein the radiation may include ionizing radiation, particularly gamma radiation irradiated by commonly used linear accelerators or radionuclides. The radiotherapy to tumor by radionuclides may be achieved externally or internally. The composition may be preferably administered one month before the irradiation, particularly 10 days or one week before the irradiation. In addition, it is favorable to continue administration of the composition between the first and the last irradiation. The administration amount of microRNA, amount of irradiation, and intermittency of irradiation may be varied according to parameters including the kind and location of cancer, and patient's response to chemotherapy or radiotherapy. And, the radiotherapy of the present invention may include brachytherapy, radionuclide therapy, external beam radiation therapy, thermal therapy (cryoablation hyperthermia), radiosurgery, charged-particle radiotherapy, neutron radiotherapy and photodynamic therapy, and the like.

The microRNA may increase radiosensitivity of cancer cells having high resistance to radiotherapy, thereby increasing the effect of radiotherapy for cancer. Furthermore, a base technology for development of new pharmaceuticals may be provided by control of gene expression through microRNA manipulation or studies on diseases other than cancer occurring due to defect in metabolism or function, and novel technology in the field of BT may be combined with radiation to advance radiation technology and utilize as next generation radiation reaction control technology.

Hereinafter, the present invention will be explained in detail with reference to Examples. However, these examples are only to illustrate the invention, and the present invention is not limited thereto.

Example 1

Cell Culture

Brain tumor cell line, glioblastoma U251 cells were cultured in a humidified chamber supplied with 5% $CO_2$ using DMEM medium containing 10% fetal bovine serum (FBS) and 1% penicillin-streptomycin.

Example 2

Transformation of Cells $2 \times 10^6$ U251 cells were inoculated on each 60 mm plate, and on the next day, to enhance expression of microRNA, the cells were treated with siPORT NeoFX™ (Ambion, Austin, Tex.) and precursor forms of each microRNA, pre-miR-7 (50 nM), pre-miR-26b (100 nM), pre-miR-203 (100 nM), pre-miR-200c (100 nM), and allowed to stand for 48 hours so that each microRNA may be introduced into the cells to induce transformation. The microRNA overexpressed through transformation was confirmed by quantitative real time PCR analysis.

Example 3

Irradiation

U251 cells were irradiated at 6 Gy using Gammacell Elite (dose rate: 3 Gy/min) with Cs gamma-ray source.

Example 4

Confirmation of Change in microRNA Expression in Transformed U251 Cells

U251 cells were transformed with microRNA, and then, cell culture medium was removed, and the cells were washed with DBPS twice. And then, the cells were treated with a TRI reagent (invitrogen, U.S.) to separate total RNA. A method for separating total RNA is as follows. After treating the cells with 1 ml of TRI reagent 1 ml, to elute total RNA from nucleoprotein complex, the cells were allowed to stand at room temperature for 5 minutes. And then, 0.2 ml of an organic solvent chloroform was added per 1 ml of the TRI reagent, the mixture was vigorously shaken with hand for 15 seconds, and allowed to stand at room temperature for 3 minutes. It was centrifuged using a centrifuge at 4° C., 12,000×g for 15 minutes to obtain a total RNA layer. The obtained total RNA layer was treated with 0.5 ml of isopropanol and mixed therewith, and then, it was centrifuged at 4° C., 12,000×g for 10 minutes to obtain total RNA pellet, and washed with 75% Et-OH. After removing the 75% Et-OH, the pellet was dried at room temperature, and dissolved with DEPC-H2O. The amount and quality of total eluted RNA were measured using a spectrophotometer. The total eluted RNA was diluted to 25 ng per μl, and a real time PCR was conducted. The expression amount of mature microRNA was measured by TaqMan microRNA assays (Applied Biosystems). The real time PCR conditions include denaturation at 95° C. for 10 minutes, and then, chain reaction at 95° C. for 15 seconds, at 60° C. for 60 seconds, with 50 cycles. The real time PCR was monitored using ABI 7500 real time PCR machine. After inducing transformation of U251 cells using this method, the expression amount of mature microRNA of each microRNA was measured, and as the results, it was confirmed that microRNA-7 increased 14.8-fold, microRNA-26b increased 20.478-fold, microRNA-203 increased 71,285,641,482-fold, and microRNA-200c increased 15.298-fold (FIG. 1).

Example 5

Confirmation of Radiosensitivity Enhancing Effect of microRNA Using Cologenic Assays To prove correlationship between the expression amount of microRNA-7, microRNA-26b, microRNA-203 and microRNA-200c with radioresistance, radioresistance was measured by cologenic assay of U251 cells. First, in 6-well plates, the cells were transformed with each microRNA, and then, cultured according to radiation dose (0 Gy: 250 cells, 2 Gy: 500 cells, 4 Gy: 1000 cells, 6 Gy: 2,000 cells, 8Gy: 4,000 cells). After confirming that the cells were stably attached to the culture dish, the cells were irradiated according to radiation dose, and cultured for about 10 days to 14 days until cell colonies were confirmed with naked eyes. After forming cell colonies, the cells were fixed with a fixing agent (100% methanol), which had been stored at −20° C. for 2 hours or more, for 10 minutes, and stained with 0.4% crystal violet reagent for 30 minutes, and then, cell colonies were counted. Surviving fraction (SF) was graphed using the average number of cell colonies of 3 well culture dishes per each radiation dose, using Kaleidagraph version 3.51.

As the results, when U251 cells were transformed respectively with microRNA-7, microRNA-26b, microRNA-203 and microRNA-200c, cell viability decreased compared to control, thus confirming that radiosensitivity increased (FIG. 2).

Example 6

Confirmation of the Effect of microRNA on DNA Damage and Repair Mechanisms

To confirm the influence of microRNA-7, microRNA-26b, microRNA-203 and microRNA-200c on the mechanisms of DNA damage and repair induced by radiation, γ-H2AX foci experiment was conducted. Specifically, if DNA single strand or double strand is broken in the cells by various DNA damaging materials including gamma radiation, γ-H2AX phosphorylation occurs to produce nuclear foci in nucleus. It was used as an indicator for evaluating DNA damage repair capacity. For γ-H2AX foci experiment, transformed U251 cells were divided into a 8-well slide glass at $6 \times 10^3$ per well, irradiated by gamma ray, and then, fixed in PBS containing 4% para formaldehyde for 20 minutes, and permeabilized with PBS containing 0.1% NP-40 at room temperature for 15 minutes. After treating with blocking buffer (PBS+0.1% NP-40+10% BSA) for 30 minutes, the cells were allowed to stand with blocking buffer containing diluted anti-γ-H2AX antibody (1:500) at 4° C. for 24 hours, and then, allowed to stand with blocking buffer containing diluted FITC antibody (1:500) at room temperature for 2 hours. The cells were stained with DAPI (100 ng/ml) for 5 minutes to see nucleus. After DAPI staining, the sample was mounted, and observed using LSM 510 microscope (Carl Zeiss, Germany).

As the results, as shown in FIG. 3, relatively many cells maintained DNA damage in each microRNA-overexpressed group, compared to control. Thus, it was confirmed that microRNA-7, microRNA-26b, microRNA-203 and microRNA-200c enhance radiosensitivity of U251 cells by inhibiting repair of DNA damage induced by radiation.

What is claimed is:

1. A method for enhancing sensitivity to radiotherapy of a brain tumor patient, the method comprising:
   administering a therapeutically effective amount of at least one selected from the group consisting of microRNA-203 and microRNA-200c to the brain tumor patient; and
   enhancing the sensitivity to radiotherapy of the brain tumor patient in response to the administration.

2. The method according to claim 1, further comprising administering a therapeutically effective amount of microRNA-7.

3. The method according to claim 1, wherein the microRNA is in the form of mature microRNA or precursor microRNA.

4. The method according to claim 2, wherein the microRNA is in the form of mature microRNA or precursor microRNA.

5. The method according to claim 1, wherein the microRNA is included in an expression vector for intracellular delivery.

6. The method according to claim 2, wherein the microRNA is included in an expression vector for intracellular delivery.

7. The method according to claim 1, wherein the brain tumor is glioma.

8. The method according to claim 1, wherein the method enhances the sensitivity to radiotherapy through delay in DNA damage repair.

9. A method for enhancing sensitivity to radiotherapy of brain tumor cells, the method comprising:
   treating the brain tumor cells with at least one selected from the group consisting of microRNA-203 and microRNA-200c; and
   enhancing the sensitivity to radiotherapy of the brain tumor cells in response to the treatment.

10. The method according to claim 9, further comprising treating the brain tumor cells with microRNA-7.

* * * * *

SEQUENCE LISTING

```
<160> NUMBER OF SEQ ID NOS: 8

<210> SEQ ID NO 1
<211> LENGTH: 23
<212> TYPE: RNA
<213> ORGANISM: Homo sapiens
<220> FEATURE:
<221> NAME/KEY: misc_RNA
<222> LOCATION: (1)..(23)
<223> OTHER INFORMATION: mature microRNA-7

<400> SEQUENCE: 1
uggaagacua gugauuuugu ugu                                             23

<210> SEQ ID NO 2
<211> LENGTH: 110
<212> TYPE: RNA
<213> ORGANISM: Homo sapiens
<220> FEATURE:
<221> NAME/KEY: misc_RNA
<222> LOCATION: (1)..(110)
<223> OTHER INFORMATION: microRNA-7 precursor

<400> SEQUENCE: 2
uuggauguug gccuaguucu guguggaaga cuagugauuu uguuguuuuu agauaacuaa     60
aucgacaaca aaucacaguc ugccauaugg cacaggccau gccucuacag               110

<210> SEQ ID NO 3
<211> LENGTH: 21
<212> TYPE: RNA
<213> ORGANISM: Homo sapiens
<220> FEATURE:
<221> NAME/KEY: misc_RNA
<222> LOCATION: (1)..(21)
<223> OTHER INFORMATION: mature microRNA-26b

<400> SEQUENCE: 3
uucaaguaau ucaggauagg u                                               21

<210> SEQ ID NO 4
<211> LENGTH: 77
<212> TYPE: RNA
<213> ORGANISM: Homo sapiens
<220> FEATURE:
<221> NAME/KEY: misc_RNA
<222> LOCATION: (1)..(77)
<223> OTHER INFORMATION: microRNA-26b precursor

<400> SEQUENCE: 4
ccgggaccca guucaaguaa uucaggauag guugugugcu guccagccug uucuccauua     60
cuuggcucgg ggaccgg                                                    77

<210> SEQ ID NO 5
<211> LENGTH: 22
<212> TYPE: RNA
<213> ORGANISM: Homo sapiens
<220> FEATURE:
```

```
<221> NAME/KEY: misc_RNA
<222> LOCATION: (1)..(22)
<223> OTHER INFORMATION: mature microRNA-203

<400> SEQUENCE: 5
gugaaauguu uaggaccacu ag                                              22

<210> SEQ ID NO 6
<211> LENGTH: 110
<212> TYPE: RNA
<213> ORGANISM: Homo sapiens
<220> FEATURE:
<221> NAME/KEY: misc_RNA
<222> LOCATION: (1)..(110)
<223> OTHER INFORMATION: microRNA-203 precursor

<400> SEQUENCE: 6
guguugggga cucgcgcgcu ggguccagug guucuuaaca guucaacagu ucuguagcgc     60 aaugugaaa uguuuaggac cacuagaccc ggcgggcgcg gcgacagcga                110

<210> SEQ ID NO 7
<211> LENGTH: 22
<212> TYPE: RNA
<213> ORGANISM: Homo sapiens
<220> FEATURE:
<221> NAME/KEY: misc_RNA
<222> LOCATION: (1)..(22)
<223> OTHER INFORMATION: mature microRNA-200c

<400> SEQUENCE: 7
cgucuuaccc agcaguguuu gg                                              22

<210> SEQ ID NO 8
<211> LENGTH: 68
<212> TYPE: RNA
<213> ORGANISM: Homo sapiens
<220> FEATURE:
<221> NAME/KEY: misc_RNA
<222> LOCATION: (1)..(68)
<223> OTHER INFORMATION: microRNA-200c precursor

<400> SEQUENCE: 8
cccucgucuu acccagcagu guuuggguge gguugggagu cucuaauacu gccggguaau     60
gauggagg                                                              68
```